United States Patent [19]

Dinh et al.

[11] Patent Number: 5,101,055
[45] Date of Patent: Mar. 31, 1992

[54] PROCESS FOR PREPARATION OF BIS- AND TRIS(SILYLORGANO)AMINES

[75] Inventors: Paul C. Dinh; Peter Y. K. Lo, both of Midland, Mich.

[73] Assignee: Dow Corning Corporation, Midland, Mich.

[21] Appl. No.: 756,723

[22] Filed: Sep. 9, 1991

[51] Int. Cl.$^5$ ............................................. C07F 7/10
[52] U.S. Cl. .................................................. 556/413
[58] Field of Search ........................................ 556/413

[56] References Cited

U.S. PATENT DOCUMENTS

| | | | |
|---|---|---|---|
| 2,715,133 | 8/1955 | Speier | 556/413 |
| 2,832,754 | 4/1958 | Jex et al. | 556/413 |
| 2,920,095 | 1/1960 | Jex et al. | 556/413 |
| 4,526,996 | 2/1985 | Kilgour et al. | 556/413 |
| 4,888,436 | 12/1989 | Shiozawa et al. | 556/413 |

OTHER PUBLICATIONS

Shriner et al.. The Preparation of Palladous Oxide and its use . . . J. Am. Chem. Soc. 46:1683–1693 (1924).

*Primary Examiner*—Paul F. Shaver
*Attorney, Agent, or Firm*—William F. Boley

[57] ABSTRACT

The present invention is a process specific for the preparation of bis- and tris- amines by the contact of silylorganoamines in the presence of palladium monoxide catalyst. The process results in near quantitative conversion of the silylorganoamines to the desired bis- and tris-amines, without the need for elevated pressures and without formation of salts of ammonia and chloride.

13 Claims, No Drawings

PROCESS FOR PREPARATION OF BIS- AND TRIS(SILYLORGANO)AMINES

BACKGROUND OF INVENTION

The present invention is a process specific for the preparation of bis- and tris-amines by the contact of silylorganoamines with palladium monoxide catalyst. The process results in near quantitative conversion of the silylorganoamines to the desired bis- and tris-amines, without the need for elevated pressures and without formation of salts of ammonia and chloride.

The bis- and tris-amines formed by the present process are particularly useful as adhesion promoting agents for glass and other materials. These amines also have wide applications for fabric treatment and in personal care products.

Speier, U.S. Pat. No. 2,715,133, issued Aug. 9, 1955, describes a process for the preparation of organosilylmethylamines. The process involves heating a halogenomethylsilane with ammonia or an amine under pressure. The process is reported to produce the corresponding aminomethylsilane and the bis- derivative thereof.

Jex et al., U.S. Pat. No. 2,832,754, issued Apr. 29, 1958, provides a process for preparing trialkoxysilylpropylamine and the bis- and tris- derivatives thereof. The process involves reacting ammonia with gamma-chloropropyltrialkoxysilane, where the ammonia is present at molar excess, at a temperature of at least 90° C. and at a pressure above atmospheric pressure. The process is reported to result in about a 20 to 50 percent yield of the mono(alkoxysilylpropyl)amine. A by-product of this process is typically a salt of ammonia and chloride.

Jex et al., U.S. Pat. No. 2,920,095, issued Jan. 5, 1960, describes a process for the preparation of tris(alkoxysilylpropyl)amines. The process consists of reacting a gamma-chloropropylalkoxysilane with ammonia, under pressure, at elevated temperatures. Jex reports the proportion of the mono-, bis-, and tris(alkoxysilylpropyl)amines obtained by the reaction can be controlled by the use of varying amounts of ammonia. The smaller the mole fraction of ammonia, based on the amount of gamma-chloropropylalkoxysilane in the reactants employed, the greater the proportion of the tris(alkoxysilylpropyl)amine in the product. A by-product of this process is a salt of ammonia and chloride.

It is an objective of the present invention to provide a process which results in near quantitative conversion of silylorganoamines to the corresponding bis- and tris-amines. Furthermore, it is an objective of the present invention to provide a process that can be run at atmospheric pressure and does not result in the production of salts of ammonia and chloride.

SUMMARY OF INVENTION

The present invention is a process specific for the preparation of bis- and tris- amines by the contact of silylorganoamines with palladium monoxide catalyst. The process results in near quantitative conversion of the silylorganoamines to the desired bis- and tris-amines, without the need for elevated pressures and without formation of salts of ammonia and chloride.

DESCRIPTION OF INVENTION

The present invention is a process for the preparation of bis- and tris(silylorgano)amines. The process comprises:

(A) contacting silylorganoamines of formula $$\{R^2_a(R^1O)_{3-a}SiR^3\}_n NH_{3-n} \tag{1}$$

with particulate palladium monoxide, at a temperature within a range of about 50° C. to 300° C., and (B) isolating product silylorganoamines of formula $$\{R^2_a(R^1O)_{3-a}SiR^3\}_y NH_{3-y} \tag{2}$$

where each $R^1$ is independently selected from a group consisting of alkyl, aryl, aralkyl, and cycloalkyl radicals of less than 20 carbon atoms; each $R^2$ is independently selected from a group consisting of $R^1$, alkenyl radicals of less than 20 carbon atoms, fluoride substituted alkyl radicals of less than 20 carbon atoms, and hydrogen; $R^3$ is selected from a group consisting of divalent hydrocarbon radicals of less than 20 carbon atoms and divalent polyethers of less than 20 carbon atoms; $a=0, 1, 2,$ or 3; $n=1$ or 2; and $y=n+1$.

The present process employs palladium monoxide as catalyst to effect the formation of bis(silylorgano)amines and tris(silylorgano)amines, hereinafter referred to as bis-amine, and tris-amine, respectively. The process may be conducted using mono(silylorgano)amine (hereinafter referred to as monoamine), bis-amine, or a mixture thereof as feed material.

Silylorganoamines which can be converted to higher amines by the present process are mono-amines and bis-amines as described by Formula 1. The silylorganoamines described by Formula 1 can contain from zero to three organooxy substituents, where the organic portion of the organooxy substituent is denoted as $R^1$. Each $R^1$ can be independently selected from a group consisting of alkyl, aryl, aralkyl, and cycloalkyl radicals of less than 20 carbon atoms. $R^1$ can be, for example, methyl, ethyl, propyl, isopropyl, butyl, tertbutyl, isobutyl, pentyl, dodecyl, phenyl, tolyl, xylyl, benzyl, beta-phenylpropyl, gamma-tolypropyl, cyclopentyl, and cyclohexyl.

The silylorganoamines described by Formula 1 can contain from zero to three substituents $R^2$, where each $R^2$ is independently chosen from the group consisting of $R^1$, alkenyl radicals of less than 20 carbon atoms, fluoride substituted alkyl radicals of less than 20 carbon atoms, and hydrogen. The alkenyl radical can be, for example, vinyl or allyl. The fluoride substituted alkyl radical can be, for example, 3,3,3-trifluoropropyl or perfluoropropyl.

The silylorganoamines described by Formula 1 contain constituent $R^3$, where $R^3$ is selected from a group consisting of divalent hydrocarbon radicals of less than 20 carbon atoms and divalent polyether radicals of less than 20 carbon atoms. $R^3$ can be, for example, alkylenes e.g. methylene, ethylene, propylene, ethylidene, and isopropylidene; cycloalkylenes e.g. cycloheptylene and cyclohexylene; divalent aromatics compounds e.g. phenylene, tolylene, xylylene, and naphthylene; and divalent radicals of aralkanes of formula $-C_6H_4-R^4-$, where $R^4$ is an alkylene radical e.g. methylene, ethylene, or propylene. $R^3$ can be, for example, a polyether of formula $R^5(OR^5)_z$, where $R^5$ is an alkylene and z is an integer of 1 to 5. The divalent polyether radical can be, for example, diethylene ether.

Preferred amines, described by Formula 1, are those where $R^1$ is methyl, ethyl, or phenyl; $R^2$ is methyl or ethyl; and $R^3$ is an alkylene radical of 1 to 3 carbons. The amine described by Formula 1 can be, for example, mono(trimethoxysilylpropyl)amine, mono(vinyldimethoxysilylpropyl)amine, mono(3,3,3-trifluoropropyldimethoxysilylpropyl)amine, mono(methyldimethoxysilylpropyl)amine, bis(trimethoxysilylpropyl)amine, bis(methyldimethoxysilylpropyl)amine, mono(triethoxysilylpropyl)amine, bis(triethoxysilylpropyl)amine, mono(phenyldimethoxysilylpropyl)amine, bis(phenyldimethoxysilylpropyl)amine, and mono(trimethoxysilylmethyl, amine.

The described process can be conducted in any standard reactor for effecting contact between solids and liquids. The reactor can be, for example, a fixed-bed, a stirred-bed, or a fluidized-bed type reactor. The process can be run as a batch process or as a continuous process. Preferred is a batch process in a stirred-bed reactor.

The contact time for the amines and palladium monoxide catalyst, within the reactor, will depend upon the catalyst concentration, the reactor temperature, and whether bis-amine or tris-amine is the desired product. In general, contact times of 5 minutes to 20 hours are considered useful when the process is run as a batch process. A preferred contact time, when the process is run as a batch process, is about 15 minutes to one hour. Shorter contact times can be used, but make the process difficult to control and may result in reduced formation of the desired products. When the process is run as a continuous process, contact times of 0.2 minutes to 2 hours are considered useful. A preferred contact time, when the process is run as a continuous process, is five to 30 minutes.

Generally, shorter contact times and/or lower catalyst levels result in a greater ratio of the bis-amine to the tris-amine. Therefore, the optimum contact time will depend upon the catalyst concentration used and the desired product.

The present process is run at near atmospheric pressure. By near atmospheric pressure is meant, there is no requirement that the present process be run at a pressure above atmospheric pressure. Ammonia is a by-product of the present process and it is preferred that this gas be removed from the process and not allowed to cause pressure buildup in the reactor. Ammonia accumulation within the reactor can reduce conversion of the feed material to higher amines. Where higher amines are defined as those in which the term y of Formula 2 is greater than the term n of Formula 1.

The catalyst for the present process comprises particulate palladium monoxide. It is preferred that the particles of palladium monoxide be 95 percent or greater, by weight, palladium monoxide. Minor amounts of palladium metal and other oxides of palladium may also be present in the particles. Preferred is a form of palladium monoxide available as palladium black from Aldrich Chemical Co., Inc., Milwaukee, WI. Alternatively, the palladium monoxide may be prepared by methods similar to those described in Shriner et al., J. Am. Chem. Soc. 46: 1683-1693 (1924).

The particulate palladium monoxide may be in the form of, for example, flakes, chips, particles, powders. Preferred is when the particulate palladium monoxide has a maximum particle diameter of less than about 0.1 mm. More preferred is when the particulate palladium monoxide has a maximum particle diameter within a range of about $20\mu$ to $100\mu$.

A useful concentration of particulate palladium monoxide catalyst is within a range of about 0.1 to 2.0 g of catalyst per mole of amine compound present in the reactor. Preferred is when the catalyst is present in a range of about 0.5 to 1.5 g of catalyst per mole of amine compound present in the reactor. When the process is run as a continuous process, flow of the feed amines to the reactor can be controlled to maintain these proportions of catalyst to amine compound present in the reactor.

A useful temperature for running the present process is within a range of about 50° C. to 300° C. Preferred, is when the temperature is about 180° C. to 250° C. Most preferred is when the process is conducted at the reflux temperature of the liquid mixture comprising silylorganoamines.

Product silylorganoamines which can be prepared by the present process are bis-amines and tris-amines as described by Formula 2, where $R^1$, $R^2$, and $R^3$ are as previously described. Examples of product silylorganoamines which can be prepared by the present process are: bis(trimethoxysilylpropyl)amine, bis(vinyldimethoxysilylpropyl)amine, bis(3,3,3-trifluoropropyldimethoxysilylpropy)amine, bis(methyldimethoxysilylpropyl)amine, tris(trimethoxysilylpropyl)amine, tris(methyldimethoxysilylpropyl)amine, bis(triethoxysilylpropyl)amine, tris(triethoxysilylpropyl)amine, bis(phenyldimethoxysilylpropyl)amine, tris(phenyldimethoxysilylpropyl)amine, bis(trimethoxysilylmethyl)amine, and tris(trimethoxysilylmethyl)amine.

The desired product silylorganoamines can be isolated by standard separation methods, for example, filtration and distillation. When the process is run as a batch process, the separated particulate palladium monoxide may be reused in the process.

In order that those skilled in the art may better understand how the present invention may be practiced, the following examples are given. These examples are given for illustration only and are not meant to be limiting on the present claims.

EXAMPLE 1

3-Aminopropyltrimethoxysilane was refluxed in the presence of palladium black catalyst for six hours. The reactor consisted of a 500 ml 3-neck flask equipped with a reflux condenser, an addition funnel, a magnetic stirring bar, and a thermometer. The reactor was purged with nitrogen gas prior to addition of catalyst and reactants. Approximately 325 g of 3-aminopropyltrimethoxysilane and 3.4 g of palladium black catalyst (Aldrich Chemical Co., Inc., Milwaukee, WI) were added to the reactor. The reaction mixture was stirred and heated to about 200° C. and then, with continued stirring, refluxed for six hours. At the end of the six hour refluxing period, the reaction mixture was cooled to room temperature and analyzed by gas chromotography (GC) employing a mass spectrometer (MS) as detector. Analysis of the area under the GC-MS trace showed 19.9 area % of bis(trimethoxysilylpropyl)amine, 60.9 area % of tris(trimethoxysilylpropyl)amine, and 1.6 area % of 3-aminopropyltrimethoxysilane.

The reaction mixture (233.1 g) was filtered to remove catalyst and then vacuum distilled through a Vigreux column under 8 mm Hg to yield 44.1 g of bis(trimethoxysilylpropyl)amine and 177.4 g of tris(trimethoxysilylpropyl)amine, representing a 93% yield, based on the amount of starting 3-aminopropyltrimethoxysilane.

EXAMPLE 2

The effects of catalyst concentration and contact time was evaluated for the conversion of 3-aminopropyl-trimethoxysilane to the corresponding bis- and tris-amines. The process was conducted similar to that described for Example 1. The catalyst concentrations tested are reported in Table 1 under the heading "Cat. Conc." The catalyst concentrations are in grams (g) of catalyst per mole of 3-aminopropyltrimethoxysilane initially added to the reactor. The time at which samples were removed from the reactor for analysis are reported in the row labelled "Time(Min.)". These times are measured from the point at which the reactor initially reached 200° C. The 3-aminopropyltrimethoxysilane (1°) remaining in the reactor at each sample time as well as product bis(trimethoxysilylpropyl)amine (Bis) and tris(trimethoxysilylpropyl)amine (Tris) are reported. Product distribution is reported as area % under the GC-MS trace.

TABLE 1
Effects of Palladium Monoxide Concentration and Contact Time on Product Distribution

| Cat. Conc. | \multicolumn{9}{c}{Product Distribution (Area %) Time (Min.)} |
|---|---|---|---|---|---|---|---|---|---|
|  | 5 | 15 | 30 | 45 | 60 | 100 | 120 | 180 | 240 |
| 0.1 g/mole | | | | | | | | | |
| 1° | — | 95 | — | 91 | 89 | 82 | 79 | 71 | 58 |
| Bis | — | 0 | — | 2 | 0 | 13 | 14 | 22 | 26 |
| Tris | — | 0 | — | 0 | 0 | 2 | 0 | 0 | 2 |
| 0.375 g/mole | | | | | | | | | |
| 1° | — | 80 | 2 | 68 | 23 | 5 | 2 | 3 | — |
| Bis | — | 12 | 66 | 23 | 43 | 35 | 28 | 14 | — |
| Tris | — | 0 | 24 | 0 | 12 | 52 | 57 | 71 | — |
| 0.75 g/mole | | | | | | | | | |
| 1° | — | 19 | 25 | 5 | 10 | 7 | 1 | — | — |
| Bis | — | 56 | 66 | 25 | 50 | 21 | 16 | — | — |
| Tris | — | 14 | 5 | 52 | 29 | 59 | 70 | — | — |
| 1.5 g/mole | | | | | | | | | |
| 1° | 3 | 1 | 1 | 0 | 2 | 1 | — | — | — |
| Bis | 49 | 28 | 14 | 14 | 7 | 8 | — | — | — |
| Tris | 33 | 59 | 68 | 65 | 55 | 55 | — | — | — |

EXAMPLE 3

The ability of palladium monoxide to effect the conversion of 3-aminopropyltriethoxysilane to the corresponding bis- and tris-amines was evaluated. The process was conducted similar to that described for Example 1. Approximately 491 g of 3-aminopropytriethoxysilane was added to 1.32 g of palladium black (Aldrich Chemical Co., Inc.). The reactor temperature was raised to approximately 175° C. and refluxing of the reactor contents begun. The reactor contents was sampled at eight minutes and 60 minutes of refluxing and analyzed by GC-MS, as previously described. The results are reported in Table 2.

TABLE 2
Effects of Palladium Monoxide and Contact Time on Product Distribution

| | Product Distribution (Area %) | |
|---|---|---|
| | 8 min. | 60 min. |
| 1° | 83 | 2 |
| Bis | 12 | 25 |
| Tris | 2 | 59 |

EXAMPLE 4

The catalyst from Example 3 was recovered by filtration and the process repeated as described for Example 3. The results are presented in Table 3.

TABLE 3
Effects of Recycled Palladium Monoxide and Contact Time on Product Distribution

| | Product Distribution (Area %) | | |
|---|---|---|---|
| | 210 min. | 510 min. | 600 min. |
| 1° | 41 | 14 | 10 |
| Bis | 11 | 31 | 28 |
| Tris | 40 | 43 | 48 |

What is claimed is:

1. A process for the preparation of silylorganoamines, the process comprising:
   (A) contacting silylorganoamines of formula $\{R^2_a(R^1O)_{3-a}SiR^3\}_n NH_{3-n}$ with particulate palladium monoxide, at a temperature within a range of about 50° C. to 300° C., and
   (B) isolating product silylorganoamines of formula $\{R^2_a(R^1O)_{3-a}SiR^3\}_y NH_{3-y}$ where each $R^1$ is independently selected from a group consisting of alkyl, aryl, aralkyl, and cycloalkyl radicals of less than 20 carbon atoms; each $R^2$ is independently selected from a group consisting of $R^1$, alkenyl radicals of less than 20 carbon atoms, fluoride substituted alkyl radicals of less than 20 carbon atoms, and hydrogen; $R^3$ is selected from a group consisting of divalent hydrocarbon radicals of less than 20 carbon atoms and divalent polyethers of less than 20 carbon atoms; $a=0$, 1, 2 or 3; $n=1$ or 2; and $y=n+1$.

2. A process according to claim 1, where the particulate palladium monoxide is palladium black.

3. A process according to claim 1, where the silylorganoamine is 3-aminopropyltrimethoxysilane and the product silylorganoamine is selected from the group consisting of bis(trimethoxysilylpropyl)amine and tris(-trimethoxysilylpropyl)amine.

4. A process according to claim 1, where the silylorganoamine is 3-aminopropyltriethoxysilane and the product silylorganoamine is selected from the group consisting of bis(triethoxysilylpropyl)amine and tris(-triethoxysilylpropyl)amine.

5. A process according to claim 1, where $R^1$ is selected from a group consisting of methyl, ethyl, and phenyl radicals; $R^2$ is selected from a group consisting of methyl and ethyl radicals; and $R^3$ is selected from a group consisting of methylene, ethylene, and propylene.

6. A process according to claim 1, where the process is conducted as a batch process in a stirred-bed reactor.

7. A process according to claim 1, where the temperature is within a range of about 180° C. to 250° C.

8. A process according to claim 1, where the temperature is the reflux temperature of the silylorganoamines.

9. A process according to claim 6, where the contact time of the silylorganoamines with the particulate palladium monoxide is within a range of about 15 to 60 minutes.

10. A process according to claim 1, where the silylorganoamines are added continuously to a reactor containing the particulate palladium monoxide and contact time of the silylorganoamines with the particulate palladium monoxide is within a range of about 5 to 30 minutes.

11. A process according to claim 9, where the particulate palladium monoxide is present within a range of about 0.5 to 1.5 g per mole of silylorganoamine added.

12. A process for the preparation of silylorganoamines, the process comprising:

contacting aminopropyltrimethoxysilane with particulate palladium black, at a temperature within a range of about 180° C. to 250° C., for about 15 to 60 minutes, in a stirred batch process reactor; and obtaining product silylorganoamines selected from the group consisting of bis(trimethoxysilylpropyl)amine and tris(trimethoxysilylpropyl)amine.

13. A process for the preparation of silylorganoamines, the process comprising:

contacting aminopropyltriethoxysilane with particulate palladium black, at a temperature within a range of about 180° C. to 250° C., for about 15 to 60 minutes, in a stirred batch process reactor; and obtaining product silylorganoamines selected from the group consisting of bis(triethoxysilylpropyl)amine and tris(triethoxysilyl-propyl)amine.

* * * * *